US005112992A

United States Patent [19]

Belmonte et al.

[11] Patent Number: 5,112,992

[45] Date of Patent: May 12, 1992

[54] PRODUCTION OF POLYCARBOXYLIC ACIDS WITH HAFNIUM-ACTIVATED COBALT CATALYST

[75] Inventors: Frank G. Belmonte, Norwood Park; Kristi A. Fjare; Walter Partenheimer, both of Naperville, all of Ill.

[73] Assignee: Amoco Corporation, Chicago, Ill.

[21] Appl. No.: 710,973

[22] Filed: Jun. 6, 1991

[51] Int. Cl.[5] .......... C07C 51/265

[52] U.S. Cl. .......... 549/245; 502/102; 502/171; 502/227; 549/248; 562/416; 562/417

[58] Field of Search .......... 562/416, 417, 102, 171, 562/227; 549/245, 248

[56] References Cited

U.S. PATENT DOCUMENTS 3,562,318 2/1971 Barone et al. .......... 562/416 X
3,694,500 9/1972 Weinstein et al. .......... 562/416
4,323,699 4/1982 Norval .......... 562/416
4,500,730 2/1985 Tanaka et al. .......... 562/416
4,873,366 10/1989 Matsuda et al. .......... 562/416

*Primary Examiner*—Jose G. Dees
*Assistant Examiner*—Vera C. Clarke
*Attorney, Agent, or Firm*—Gunar J. Blumberg; William H. Magidson; Frank J. Sroka

[57] ABSTRACT

The addition of hafnium to oxidation catalysts provided by a heavy transition metal-bromine ion catalyst combination containing cobalt-manganese-bromine or manganese-bromine or cobalt-bromine and a soluble source of hafnium uniquely increases catalytic activity of the said catalyst combination for converting methyl groups on the benzene nucleus. The presence of hafnium in the total reactor contents is equal to or less than 250 parts per million by weight of the total reactor mother liquor. The solubility of the hafnium in the reactor solvent is such that reactor product cake contains less than 0.3 ppm by weight. Bromine emissions can be reduced.

15 Claims, No Drawings

PRODUCTION OF POLYCARBOXYLIC ACIDS WITH HAFNIUM-ACTIVATED COBALT CATALYST

FIELD OF THE INVENTION

The field of this invention relates to the liquid phase oxidation of di-, tri-and tetramethyl benzene compounds in the presence of a cobalt-manganese-bromine catalyst in an acetic acid medium to prepare polycarboxylic acid compounds which are thereupon hydrogenated in aqueous solution to remove soluble impurities. Activity of the transition metal-bromine catalyst is enhanced by addition of soluble hafnium compounds in amounts of less than 250 parts per million by weight (ppmw) of the total reactor mother liquor. The soluble hafnium compound in the $C_2$–$C_6$ aliphatic carboxylic acid medium, i.e. an acetic acid medium, is retained in the $C_2$–$C_6$ aliphatic carboxylic acid medium, i.e. the acetic acid or an acetic acid-water mother liquor, upon filtration and acetic acid and/or water washing of the filter cake. The aqueous slurry containing the polycarboxylic acid compounds thereby prepared is suitable for a reduction process.

This invention particularly relates to the preparation of crude terephthalic acid by oxidation of p-xylene in the presence of a soluble cobalt-manganese-bromine catalyst, the activity of the cobalt-manganese-bromine catalyst being enhanced by the presence of a soluble hafnium compound wherein hafnium is present in an amount equal to or less than about 250 parts per million by weight of the total reactor mother liquor comprising an acetic acid-water solution. The crude terephthalic acid is recovered from the mother liquor by filtration and is acetic acid and/or water washed to remove acetic acid and water soluble impurities. An aqueous slurry thereby prepared is suitable for a reduction process. In one aspect, this invention relates to a catalyst composition whose activity is enhanced by a soluble hafnium compound in the oxidation of p-xylene to crude terephthalic acid. The crude terephthalic acid is recovered by filtration and is acetic acid and/or water washed to remove residual acetic acid and water-soluble impurities. An aqueous slurry thereby prepared is suitable for a reduction process in the presence of a palladium-on-carbon catalyst, residual catalyst-deactivating hafnium compounds having been removed from the crude terephthalic acid before the reduction procedure.

BACKGROUND OF THE INVENTION

The possibility of using liquid phase instead of vapor phase oxidation for the preparation of benzene carboxylic acids was first indicated by the disclosure in U.S. Pat. No. 2,245,528 of the catalysis provided by transitional or variable valence metals, especially cobalt, in a liquid phase of saturated lower aliphatic acid at temperatures from 100° to 320° C. and pressures to maintain the liquid phase of the aliphatic acid. Such catalysis, according to said patent, was advantageously promoted by the use of a ketone such as methylethyl ketone or aldehyde such as acetaldehyde. Unfortunately such aldehyde or ketone promoted variable valence metal catalysis was useful only for converting mono-, di- and tri-methylbenzenes to their respective benzene monocarboxylic acids: benzoic, toluic and dimethyl benzoic acids. Two separate, later and somewhat parallel lower temperature (80°–100° C.) modifications of the aldehyde or ketone promoted cobalt catalysis in liquid phase of acetic acid did provide commercially feasible conversion of xylenes to phthalic acids, especially p-xylene to terephthalic acid but only at the expense of using rather high concentrations of cobalt and added quantities of acetaldehyde or methylethyl ketone promoter which were oxidized to acetic acid.

For the liquid phase oxidation of di-, tri- and tetramethylbenzenes with molecular oxygen, it has been discovered that hafnium compounds are unique among compounds of the Group IV metals in being substantially more soluble in solutions of di-, tri-, and tetramethylbenzenes and $C_2$ to $C_6$ monocarboxylic acids than compounds of the other Group IV metals. Group IV metals activate Co/Br, Mn/Br or Mn/Co/Br catalysts but hafnium is unique in that hafnium compounds do not precipitate as readily from the liquid phase reaction mixture under reaction conditions or in the presence of reaction products as readily as compounds of other metals of Group IV in the presence of reaction products. Reaction products accordingly are not contaminated by the presence of hafnium compounds.

In reference to the enhancement of catalytic activity by hafnium, there are two aspects. First is the increase in activity of cobalt-bromine, manganese-bromine or manganese-bromine-cobalt catalyst systems by a factor much greater than would be expected by increase in amounts of either manganese and/or cobalt equivalent to the amount of hafnium employed. The second is manifested by the longer sustained initial rapid rate of oxygen consumption when hafnium is a member of the system of catalysis than when the catalyst system comprises cobalt bromine, manganese-bromine or manganese-bromine-cobalt.

Such functions and attributes of hafnium as soluble catalyst compounds in the liquid phase oxidation of di-, tri-, and tetramethylbenzenes are indeed unobvious when the character and nature of these functions and attributes of hafnium are considered and compared to manganese and/or cobalt and other Group IV metals. Manganese and cobalt have been known for some time to have the highest oxidation potential of the transition metals characterized in U.S. Pat. No. 2,425,528 as oxidation catalysts. The Group IV metals are not generally considered to be transition metals in a redox system as are cobalt, manganese and other of such metal oxidation catalysts because of their non-variable valence states in oxidation systems.

It is recognized that combinations of cobalt with Group III A or Group IV A metals, as taught in U.S. Pat. No. 3,299,125, are beneficial systems of catalysis for the liquid phase oxidation of alkyl-substituted aromatic hydrocarbons containing two or more alkyl groups which are not adjacent to each other in the ortho position on the aromatic nucleus. Thus the disclosed system of catalysis comprising cobalt and any metal of the Group III A or Group IV A, particularly preferred being scandium, yttrium, neodymium, thorium, zirconium and hafnium, among others, is taught as ineffective for di- and trialkylbenzene such as o-xylene or pseudocumene. Reported yields in U.S. Pat. No. 3,299,125 of terephthalic acid product using a hafnium catalyst range from about 55% to about 76%.

It is also known that, as U.S. Pat. No. 3,562,318 teaches, in the liquid phase oxidation of alkyl-substituted aromatic compounds in the presence of aldehyde or ketone side chain oxidation inhibitors or promoters, beneficial effects are obtained with a cobalt catalyst in combination with one or more metals of the group consisting of Al, Zn, La, Nd, Zr, B or Mg.

It is further known that Canadian Patent No. 1,146,588 teaches a process for preparing aromatic carboxylic acids by oxidation of an alkyl-aromatic hydrocarbon in the liquid phase in the absence of an aliphatic carboxylic acid by means of a gas containing molecular oxygen and in the presence of a catalyst consisting of a soluble cobalt compound and a soluble zirconium or hafnium compound. Atomic ratios of zirconium to cobalt or hafnium to cobalt are ratios lower than 1:5, preferably lower than 1:10. Aromatic carboxylic acids prepared thereby suffer from the drawback of containing many impurities, including aldehydes, alcohols and esters as by-products, which reduces the desirability of the proposed process.

Japanese Patent JP55017348 teaches oxidation of p-tolualdehyde to terephthalic acid in the presence of a metal catalyst selected from a group including zirconium and hafnium and a bromine compound whereby a mineral acid is added to the reaction to effect the oxidation. Also, Japanese Patent JP48096545 teaches a process for oxidizing p-xylene to terephthalic acid in the presence of cobalt and zirconium or hafnium wherein the zirconium or hafnium is present in an amount of from 0.01% to 1% by weight of the cobalt present.

Accordingly, as noted above, the above patents disclose the use of hafnium as a catalyst or co-catalyst in the oxidation of alkyl-substituted aromatic compounds but only with the disadvantage of obtaining relatively low product yields when using hafnium as a catalyst, or product contaminated with many by-product impurities, or of using high concentrations of cobalt promoted with quantities of aldehyde or ketone in the absence of hafnium as a co-catalyst.

The disadvantages of using cobalt in the presence of an aldehyde or ketone or hafnium are overcome by our novel process wherein hafnium is used to activate the cobalt-manganese-bromine catalyst. Our novel process is effective in converting di- or polymethylbenzenes to their corresponding aromatic acids, wherein the mole ratio of hafnium to cobalt, manganese, and bromine is about 1:20 to about 1:600, by weight, preferably, about 1 part hafnium to about 50 parts total cobalt plus manganese plus bromine.

For the liquid phase oxidation of di-, tri and tetramethylbenzenes with molecular oxygen, it has been discovered that hafnium is particularly useful for substantially enhancing the activity of a catalyst system comprising cobalt, manganese and bromine. Acetic acid and/or water-soluble forms of hafnium are especially useful for substantially enhancing the activity of a catalyst system comprising cobalt, manganese and bromine in that acetic acid and/or water-soluble hafnium compounds do not precipitate upon crystallization on di- and polycarboxylic acids obtained from the oxidation reaction, as for example, crystals of terephthalic acid which require further purification before use in preparation of various polymers.

Cobalt is the most expensive component in a cobalt-manganese-bromine catalyst system, approximately ten to fifteen times more expensive than manganese. Therefore, there is great economic incentive to reduce the amount of the oxidation catalyst. Our novel process has succeeded in doing just that by decreasing the concentration of the catalyst components of cobalt and manganese and bromine by a calculated 22%, see Example II. A novel feature of hafnium as a catalyst activator in the oxidation of polymethylbenzenes to the corresponding polycarboxylic acids is that much less catalyst is required to obtain satisfactory yields. Our novel process can also reduce the amount of bromine required, see Example VII. It may also be possible to reduce individually the amount of cobalt and/or manganese required.

Hafnium has been found to be an effective promoter for the cobalt-manganese-bromine catalyst systems for the oxidation of polymethylbenzenes to the corresponding polycarboxylic acids. The term "activation", as used herein, means the ability of a catalyst component to increase the rate of oxidation of polymethylbenzenes to the corresponding polycarboxylic acids. A further novel feature of hafnium as a catalyst activator in the oxidation of polymethylbenzenes to the corresponding polycarboxylic acids is that acetic acid and/or water-soluble compounds of hafnium demonstrate greater acetic acid and/or water solubility under oxidation conditions and/or presence of polycarboxylic acids than do compounds of other elements such as zirconium, molybdenum, vanadium, titanium, and chromium when used in ratios which activate cobalt in the oxidation reaction. Contamination of the resulting polycarboxylic acid product by residual catalyst components is thereby significantly reduced.

Polymethylbenzenes such as o-, m-, and p-xylenes can be oxidized to phthalic acid or phthalic anhydride, isophthalic acid, and terephthalic acid by the process of this invention. Durene can be oxidized to pyromellitic acid or to the pyromellitic anhydrides. Pseudocumene can be oxidized to trimellitic acid or trimellitic anhydride.

Terephthalic acid is produced by a liquid phase oxidation of p-xylene and/or p-toluic acid in a solvent comprising an aliphatic carboxylic acid such as acetic acid. Terephthalic acid is of great commercial importance and is widely used for the production of various polymers, such as fiber-forming polyesters. A process for preparing polyesters of terephthalic acid, particularly polyethylene terephthalate, comprises a direct condensation of terephthalic acid with the respective polyalcohol. For example, terephthalic acid is reacted with ethylene glycol to form bis($\beta$-hydroxyethyl) terephthalate which is then polymerized in a second stage. This direct condensation process is simpler than other known methods such as transesterification of dimethyl terephthalate with the appropriate glycol. However, the direct esterification requires the use of highly purified terephthalic acid. In order to be suitable for the production of polyester fibers, terephthalic acid must be substantially free of any contaminants which lower the melting point of the polyester and/or cause coloration of the polyester. In fact, some impurities which are contained in crude terephthalic acid are color-forming precursors of the terephthalic acid. Additionally, some impurities act as chain terminators in the process to prepare polyesters.

All these impurities have not yet been identified. However 4-carboxybenzaldehyde which is an intermediate oxidation product and which in the following is abbreviated as 4-CBA, generally is found in crude terephthalic acid. It is known that the degree to which coloration in the polyester is induced is less if the 4-CBA content of the terephthalic acid is low. While pure 4-CBA itself does not necessarily promote coloring during polymerization, this impurity is a convenient tracer for evaluating the degree to which terephthalic acid has been refined. A process which can reduce the 4-CBA content of terephthalic acid reduces also the content of color-forming precursors.

From U.S. Pat. No. 3,584,039 issued to Delbert H. Meyer, incorporated by reference, it is known that fiber-grade terephthalic acid may be prepared by purifying crude terephthalic acid by means of a reduction procedure. The process is essentially comprised of treating an aqueous solution of crude terephthalic acid with hydrogen in the presence of a supported or unsupported Group VIII metal catalyst, whereby the metal and the support are insoluble in the solution under the working conditions. By this process, the amounts of 4-CBA and other coloring impurities contained in terephthalic acid are reduced by formation of removable products. Purified terephthalic acid is then recovered by crystallization, filtration to recover the crystalline product, and drying.

As noted above, the oxidation of p-xylene can be in the presence of a hafnium compound as a co-catalyst for the cobalt-manganese-bromine catalyst. However, it is considered that hafnium may also act as a catalyst poison to the supported or unsupported Group VIII metal catalyst, typically palladium, useful in the reduction procedure to prepare fiber-grade terephthalic acid. Additionally, it is also known that the aliphatic carboxylic acid which comprises the solvent for the liquid phase oxidation of p-xylene and/or p-toluic acid can act as a poison for the reduction catalyst. Methods have been proposed for replacement or extraction of the aliphatic carboxylic acid, such as acetic acid, from the oxidation effluent with water. For example, U.S. Pat. No. 3,839,436 teaches contacting an oxidation slurry with water wherein water is introduced into the bottom of a displacement zone to contact the oxidation effluent in a vertical chamber to effect precipitation of the product acid through the column of water and to remove an aqueous slurry suitable for catalytic purification from the bottom of the column. Concurrent removal of at least a portion of the hafnium component of the soluble hafnium cobalt-manganese-bromine oxidation catalyst by extraction with water can therefore result.

Water extraction of aliphatic carboxylic acids such as acetic acid and a co-catalyst such as hafnium can therefore comprise a positive method to reduce the concentration of acetic acid and hafnium in the crude terephthalic acid.

It is therefore an object of this invention to provide a co-catalyst to reduce the amount of cobalt component in the oxidation catalyst. It is a further object of this invention to provide a hafnium co-catalyst in the oxidation of polymethylbenzenes to the corresponding polycarboxylic acids wherein much less cobalt is required to obtain satisfactory yields. Moreover, it is an object of this invention to provide a hafnium co-catalyst which is sufficiently acetic acid and/or water soluble to be at least partially removed or extracted from crystals of crude terephthalic acid before the crude terephthalic acid is slurried in water for a reduction process.

SUMMARY OF THE INVENTION

A process is disclosed for oxidizing polymethylbenzenes with molecular oxygen to benzene polycarboxylic acids under liquid phase conditions wherein the process comprises conducting the oxidation in the presence of a $C_2$–$C_6$ aliphatic carboxylic acid or a mixture of a $C_2$–$C_6$ aliphatic carboxylic acid and water, wherein the carboxylic acid is a solvent for the reaction and for a hafnium-cobalt-manganese-bromine catalyst at temperatures in the range of from about 100° C. to about 250° C. in the presence of a catalyst and a catalyst consisting essentially of a source of soluble hafnium and a catalyst system comprising cobalt, manganese and bromine wherein the source of hafnium is an acetic and/or water-soluble compound and the hafnium is an effective promoter for the cobalt-manganese-bromine catalyst system and wherein the gram-atom ratio of hafnium to cobalt plus manganese and bromine is in the range of from about 1:20 to about 1:600, ratio of cobalt to manganese preferably is in the range of from about 4:1 to about 0.2:1.0, and amount of said hafnium present in total reactor contents is equal to or less than about 250 parts per million by weight of the total mother liquor.

DETAILS OF THE INVENTION

In one embodiment of this invention, an alkyl aromatic, such as a p-xylene and/or p-toluic acid, is oxidized in acetic acid medium with molecular oxygen in the presence of a catalyst system consisting of cobalt, manganese, bromine and hafnium wherein the hafnium is present to enhance the activity of the cobalt-manganese-bromine catalyst components. Although it is well-known in the prior art to use a cobalt-manganese-bromine catalyst to oxidize p-xylene to terephthalic acid, it has not been previously known that the presence of hafnium in the catalyst system in an amount equal to or less than 250 parts per million by weight of the total reactor mother liquor would substantially enhance the activity of the catalyst system whereby the amount of catalyst may be reduced such that much less catalyst is required to obtain satisfactory yields. The source of the hafnium component is such that the concentration of the hafnium component remaining on crude terephthalic acid crystal as residue, after the crystals have been washed with acetic acid or water, or a solution of acetic acid and water, is less than 0.3 ppmw.

A novel feature of the instant invention therefore is that it has been found that use of hafnium as a cobalt-manganese-bromine co-catalyst reduces the total amount of catalyst (cobalt-manganese-bromine) necessary. As noted earlier, since cobalt is the most expensive component in the cobalt-manganese-bromine catalyst system, there is great economic incentive to replace or reduce the cobalt component in the oxidation catalyst. A further novel feature of the instant invention is that it has also been found that use of hafnium in a cobalt-manganese-bromine catalyst system can reduce separately the bromine component, and potentially, the cobalt or manganese components as well. In the case of bromine, the reduction of bromine in the catalyst system reduces equipment corrosion with consequent economic advantage. In the case of manganese, the reduction of manganese in the catalyst system can reduce possible contamination of purified terephthalic acid (PTA), the desired product, because of catalyst carryover in product.

It has been found, see Example II, that the presence of 30 parts per million by weight (ppmw) of hafnium in the reactor mother liquor in continuous oxidation of p-xylene in the presence of a cobalt-manganese-bromine catalyst can allow a 12 wt % reduction in the amount of the cobalt-manganese-bromine catalyst without entailing the development of increased production of impurities, as measured by the production of 4-carboxybenzaldehyde (4-CBA), or loss of catalyst activity. Catalyst activity is increased despite a 12 wt % decrease in the amount of cobalt-manganese-bromine catalyst in the presence of 30 ppmw of hafnium in the reactor mother liquor.

It has been found, see Example III, that hafnium compounds are more soluble than zirconium compounds in an acetic acid-water mixture in the presence of oxidation by-products of p-xylene such as trimellitic acid and pyromellitic acid. As is taught in U.S. Pat. No. 3,920,735, zirconium is known to enhance activity of transition metal-bromine catalysis of di- and trimethylbenzene oxidation in liquid phase. However, it has been considered that in further processing, zirconium compounds and hafnium compounds can have a deleterious effect upon the activity of the catalyst used in the reduction procedure to prepare purified terephthalic acid from crude terephthalic acid. Surprisingly, it has been found that the solubility of hafnium compounds as a soluble component of a hafnium-cobalt-manganese-bromine catalyst reduced the possibility of contamination of the terephthalic acid product by hafnium to below detectable levels by inductively coupled plasma (ICP) methods, i.e. below 0.3 ppmw. Comparable test procedures wherein zirconium compounds were employed in zirconium enhanced activity of transition metal-bromine catalysis of di- and trimethylbenzene oxidation in liquid phase indicated that contamination of the terephthalic acid product occurred in measurable levels, as measured by ICP methods.

It has been found, see Example VI, that significant decreases in the production of bromine compounds in the vent gas occur in the oxidation of p-xylene in the presence of a soluble hafnium compound and a catalyst system comprising cobalt-manganese-bromine.

Decreases in decomposition of oxidation reactants, as measured by production of carbon oxides may be obtained by use of a hafnium-cobalt-manganese-bromine catalyst.

Water is produced as a by-product of the oxidation of p-xylene to terephthalic acid. The presence of water in the oxidation reaction decreases the activity of a cobalt-manganese-bromine catalyst by reducing the rate of oxidation as measured by oxygen utilization. A surprising effect of the incorporation of a hafnium compound into the cobalt-manganese-bromine catalyst is the continued activity in the presence of water, as is exemplified in Example IV.

For the present invention the ratio of hafnium to total conventional metal oxidation catalysts (Co, Mn and Co-Mn) is in the range of respective metals, i.e. Hf: total conventional metals, of about 1:10 to about 1:750 on a milligram atom basis, with the provision that total Hf present is less than or, at most, equal to 250 ppmw by weight of the total reactor mother liquor comprising an acetic acid and/or water solution. The ratio of total metals, Hf plus conventional oxidation metals to bromine is in the range of from about 0.1:1.0 to about 10.0:1.0 on the milligram atom basis. Thus for each gram-mole of m-or p-xylene in the oxidation there is used from 0.008 to 0.44 milligram atom hafnium, 1.0 to 20.0 milligram atoms total of cobalt-manganese, or manganese, or cobalt, and from 0.2 to 10.0 milligram atoms bromine.

Hafnium can be added to the reaction in any form soluble in the reaction mixture or reaction solvent when acetic acid is used as the reaction solvent. Conveniently, hafnium can be added as a bromine compound, consistent with the amount of bromine required by the composition of the catalyst.

The source of molecular oxygen for the hafnium enhanced oxidation of this invention can vary in $O_2$ content from that of air to oxygen gas. Air is the preferred source of molecular oxygen for oxidations conducted at temperatures of 100° C. and above up to 275° C. For oxidations conducted with molecular oxygen the preferred temperatures are in the range of 100° C. to 200° C. The minimum pressure for such oxidations is that pressure which will maintain a substantial liquid phase, 70-80%, of the reaction medium either neat di- or trimethylbenzene or such methylbenzene and 70-80% of the acetic acid. The acetic acid solvent, when used, can amount to 1-10 parts on weight basis per part of the di- or trimethylbenzene. The methylbenzene and/or acetic acid not in the liquid phase because of vaporization by heat of reaction is advantageously condensed and the condensate returned to the oxidation as a known means for removing heat and thereby temperature controlling the exothermic oxidation reaction. Such vaporization of methylbenzene reactant and/or acetic acid solvent is also accompanied by vaporization of lower boiling by-product water. When it is desired to take advantage of the known benefits of control of water concentration in oxidation, condensed water is separated from the condensate before its return to the oxidation reaction by any one of the well known means for accomplishing such separation of water; for example, by phase separation of liquid water from the methylbenzene condensate or by distillative separation of water from acetic acid.

In the examples which follow, the continuous oxidations were conducted in a pilot plant two-stage reactor to simulate commercial operation. The reactors were stirred titanium autoclaves, each having a water-cooled overhead condenser and condensate reflux return to the autoclave. Both oxidation reactors also had means for venting the exhaust gaseous mixture (nitrogen, unused or excess oxygen, oxides of carbon, water vapor and vapor of acetic acid) and analytical means for determining the oxygen, carbon dioxide and carbon monoxide contents of exhaust samples on an acetic acid-free dry basis. Where appropriate, concentrations are expressed in moles (hereinafter designated M).

A batchwise oxidation was conducted by charging all of the catalyst components, the polymethylbenzenes, and the acetic acid solvent, sealing the reactor and pressuring the reactor to the desired pressure with nitrogen and heating the reactor contents to the desired temperature.

The following examples are submitted to illustrate the invention but are not intended to limit the scope of the invention.

EXAMPLE I

A series of hafnium-activated continuous oxidations of p-xylene were made in a pilot plant to prepare terephthalic acid. The pilot plant consists of two reactors, a primary reactor and a secondary reactor, both 2-liter titanium reactors equipped with water-cooled overhead condensers with condensate reflux return to each reactor.

Following the condensation system, there are means for venting the exhaust gaseous mixture (nitrogen, unused or excess oxygen, oxides of carbon, water vapor, and vapor of uncondensed acetic acid and some of the unreacted xylene) and analytical means for determining the oxygen, carbon dioxide and carbon monoxide contents of exhaust sample on acetic acid-free dry basis.

The exhaust sample flows through three cooled (e.g. dry ice-acetone cooled) traps before analysis for $O_2$, $CO_2$ and CO.

Two stage oxidations were conducted to more accurately simulate commercial operation. Two base case oxidations were performed using a cobalt-manganese-bromine catalyst. Two oxidations were performed where hafnium was added at a level to afford 30 ppmw in the reactor mother liquor. In one of the hafnium oxidations, the catalyst package comprising cobalt-manganese-bromine was reduced by 12 wt %.

A mixture containing the p-xylene, acetic acid solvent and catalyst components was continuously added to the primary reactor (primary oxidation). The composition of the mixture is given in Table I. From the primary reactor the slurry is transferred to the secondary reactor (secondary oxidation). The effluent from the secondary reactor is stored in a sample collection vessel. A sample is also obtained of the primary reactor effluent. Both reactors are mechanically agitated. Oxygen is provided to each reactor by the addition of air or a synthetic mixture of nitrogen and oxygen. The oxygen depleted air from each reactor containing volatile oxidation by-products is vented. A portion of the slurry from each reactor was filtered to form a cake which was washed with an acetic acid-water mixture. The important kinetic performance data are provided in Table II. Data as to oxidation results are provided in Table III. Using ICP (Inductively Coupled Plasma) no hafnium could be detected in the product cakes that were washed with an acetic acid-water solution. The detectability limit for the analysis is about 0.3 ppmw.

TABLE I

| Feed Mix Composition[1,2] | |
|---|---|
| p-Xylene: | 35.95 lb |
| Acetic Acid: | 81.34 lb |
| $Co(OAc)_2 4H_2O$: | 88.20 g |
| $Mn(OAc)_2 4H_2O$: | 93.11 g |
| Hydrobromic Acid (48%): | 56.24 g |
| Water: | 793.40 g |
| $Hf(Br)_4$: | 4.09 g |

[1]Feed mix rate 12.04 lb/hour
[2]Primary oxidation air rate 180.0 SCFH (21% $O_2$). Secondary oxidation air rate 21.0 SCFH (7.99% $O_2$).

TABLE II

| Kinetic Parameters | Primary Oxidation | Secondary Oxidation |
|---|---|---|
| Temperature: | 382.2° F. | 367.2° F. |
| HCTP[1]: | 0.150 | 0.303 |
| Mother Liquor Cobalt Concentration | 428 ppmw | 436 ppmw |
| Manganese/Cobalt: | 1.09 (M/M) | 1.08 (M/M) |
| Bromine/Metals: | 0.456 (M/M) | 0.449 (M/M) |
| Solvent Ratio: | 2.95 | 2.92 |
| Oxygen Partial Pressure: | 2.14 psi | 4.15 psi |
| Solvent Water Concentration | 13.8 wt. % | 14.3 wt. % |
| Solvent Residence Time | 68.3 min | 34.8 min |
| Agitator Speed: | 1370 | 1000 |
| Pressure: | 204 psig | 194 psig |

[1]HCTP = Hydrocarbon throughput (Mpx/hr ft$^3$).

TABLE III

| Oxidation Results | Primary Oxidation | Secondary Oxidation |
|---|---|---|
| Slurry 4-CBA: | 2563 ppmw | 785 ppmw |
| Slurry Optical Density($OD_{340}$) | 1.72 | 1.23 |

TABLE III-continued

| Oxidation Results | Primary Oxidation | Secondary Oxidation |
|---|---|---|
| Carbon Oxides Production: | 0.215 ($MCO_x$/MpX) | 0.025 ($MCO_x$/MpX) |
| Methyl Acetate Production: | 0.1111 (M/MpX) | 0.0008 (M/MpX) |
| Cake Hafnium Concentration: (Determined by ICP) | <0.3 ppmw | <0.3 ppmw |

The above data indicate that oxidation of p-xylene with a hafnium-cobalt-manganese-bromine catalyst to prepare terephthalic acid, followed by an acetic acid-water wash, can result in a product containing less than 0.3 ppmw of hafnium.

EXAMPLE II

In the procedure described in Example I, four continuous oxidations of p-xylene to terephthalic acid were completed. Two base case oxidations were performed wherein the catalyst comprised a conventional cobalt-manganese-bromine composition. Two oxidations had hafnium added to give a level of 30 ppmw in the reactor mother liquor. In one of the hafnium additions, the conventional cobalt-manganese-bromine catalyst was reduced by 12 wt % without loss of catalyst activity. The data for the production of 4-carboxybenzaldehyde (4-CBA) and carbon oxides ($CO_x$) are in Table IV.

TABLE IV

| | 4-CBA (ppmw) | $CO_x$ (moles/moles pX) |
|---|---|---|
| Base Case (Co/Mn/Br) | 2888 | 0.205 |
| 30 ppmw Hf + Co/Mn/Br | 2191 | 0.229 |
| 30 ppmw Hf + Co/Mn/Br but 12 wt % less Co/Mn/Br | 2563 | 0.215 |
| 30 ppmw Hf + Co/Mn/Br but 22 wt % less Co/Mn/Br (calc.) | 2880 (target) | 0.204 (calc.) |
| Base Case (Co/Mn/Br) | 2846 | 0.204 |

The above data indicate the hafnium activated the oxidation. The 4-CBA concentration decreased by 676 ppmw (23.6%). The decrease in the Co/Mn/Br package resulted in a 304 ppmw (10.6%) reduction in the 4-CBA. The $CO_x$ production increased but less than the oxidation where the catalyst package was not reduced. Higher $CO_x$ production occurred because of higher conversion rate. It is calculated that, with the addition of 30 ppmw hafnium to the reaction mother liquor, the conversion level of the base case, as measured by the presence of 4-CBA, can be obtained by a 22% reduction in weight of total catalyst.

EXAMPLE III

Solubility of hafnium compounds, i.e., hafnium bromide, was determined in acetic acid-water mixtures in the presence of trimellitic acid and pyromellitic acid. Hafnium tetrabromide, 0.0012M, was heated in a 20% water-acetic acid solution to reflux. Trimellitic acid (0.71M) was added. The solution remained clear. The procedure was repeated with zirconium tetrabromide but precipitation occurred. The results were compared with two filtrates comprising pyromellitic acid from oxidation of durene which had been oxidized in the presence of hafnium or zirconium. Results are in Table V.

TABLE V

| Solubility of Hafnium and Zirconium Tetrabromides in Acetic Acid-Water Mixtures in Presence of Trimellitic Acid and Pyromellitic Acid | % Soluble | |
|---|---|---|
| | Hafnium | Zirconium |
| Metal + Trimellitic Acid in 20% $H_2O$ - HOAc at 100° C. | 100% (a) | <100% |
| Metal + Trimellitic Acid in 20% $H_2O$ - HOAc at 25° C. | 36% (b) | 11% |
| Metal in Filtrate after Durene Oxidation | 32% | 6.9% |

(a) Experiment repeated twice
(b) Same experiment as in (a) except solution was cooled and solids filtered off The above data indicate that on a molar basis 36% of the hafnium remained in solution but only 11% of the zirconium did. Also 32% of the hafnium remained in solution after the durene oxidation but only 6.9% of the zirconium did.

EXAMPLE IV

The following example illustrates the poisoning effect that water has on the activity of a cobalt-manganese-bromine catalyst and the effect which the presence of hafnium has as a co-catalyst metal with a cobalt-manganese-bromine catalyst. The deactivating effect upon the catalyst activity was evaluated because water is a product of the oxidation of p-xylene or any alkyl aromatic compound.

An initial solution was prepared which contained 15.0 ml p-xylene, 75.0 ml acetic acid, 0.125 grams cobalt (II) acetate tetrahydrate, 0.123 grams manganese (II) acetate tetrahydrate, and 0.103 grams sodium bromide. The reactor was a glass reactor operated at atmospheric pressure. The reaction was initiated with a flow of 50 ml/min of air at 100° C. After the initial rate of reaction had become constant, water was added to the reactor at a rate of 0.21 ml/min by means of a syring pump. The rate of oxygen uptake was continuously monitored by measuring the vent gas for oxygen by gas chromatography. The results are in Table VI.

TABLE VI

Effect of Water on p-Xylene Oxidation In Presence of Hafnium

| Water Added Vol. % | No Addition of Hafnium: Hf Conc. | No Addition of Hafnium: ml $O_2$ Reacted per minute | Hafnium Added, 40 ppmw: Hf Conc. | Hafnium Added, 40 ppmw: ml $O_2$ Reacted per minute |
|---|---|---|---|---|
| 0.00 | 0.0 | n.d. | 40 | n.d. |
| 2 | 0.0 | 4.1 | n.d. | 5.3 |
| 5 | 0.0 | 1.7 | n.d. | 3.5 |
| 10 | 0.0 | 0.6 | 35 | 1.3 |
| 15 | | | 33 | 1.8 |
| 20 | | | 32 | 2.1 |
| 25 | | | 30 | 1.6 |
| 30 | | | 29 | 1.2 |
| 35 | | | 27 | |

Note:
n.d. - not determined

The above data indicate that in the absence of hafnium, and the presence of water in amounts of about 15 vol %, the oxidation essentially ceases in the presence of a cobalt-manganese-bromine catalyst. However, in the presence of 25 vol % of water and 30 ppmw of hafnium, the oxidation continues.

EXAMPLE V

Durene was oxidized in a pilot plant batch reaction to pyromellitic acid as described in the U.S. Pat. No. 4,719,311 issued to W. Partenheimer. In one case zirconium tetrabromide was used as the zirconium source in which a 68% pyromellitic acid yield was obtained. The oxidation was repeated using hafnium tetrabromide in place of zirconium tetrabromide. A 75% yield of pyromellitic acid was obtained. When the reactor effluent was cooled to room temperature and filtered, 11% of the zirconium remained soluble while in the other oxidation 36% of the hafnium remained soluble. This illustrates that hafnium can activate at least as strongly as zirconium, but much less of the hafnium deposits on the product cake since more hafnium is found in the filtrate.

EXAMPLE VI

In the procedure of Example I, two oxidations of p-xylene were made in a single-stage pilot plant and compared with an oxidation of p-xylene using a hafnium-activated cobalt-manganese-bromine catalyst system. Ratio of manganese to cobalt in each oxidation was 0.9 to 1.0. The oxidations were made in one stage, in a primary oxidation stage. The purpose of the comparison runs was to determine the effect of the hafnium-activated catalyst upon the production of bromine compounds in the oxidation of the p-xylene. The effect of the hafnium-activated cobalt-manganese-bromine catalyst was to reduce the production of bromine compounds, as measured by presence of methyl bromide in the vent gas. The data from each oxidation were adjusted to a standard content of 2800 ppmw of 4-CBA for comparison upon the same basis using catalyst concentration of cobalt and manganese as the means of adjustment. Concentration of hafnium in mother liquor was 30 ppmw. The adjustments were made upon the basis of previously derived correlations.

One oxidation was made as a control wherein the mole ratio of bromine to the mole ratio of total metals present, manganese, plus cobalt, was 1.0:2.13. Methyl bromide production in the vent gas was 10.1 ppmw.

One oxidation was made wherein concentration of bromine was lowered as a component of the cobalt-manganese-bromine catalyst. The absolute concentrations of manganese and cobalt were increased. The mole ratio of bromine to total metals present, cobalt plus manganese, was 1.0:3.85. Methyl bromide emission was 12.7 ppmw.

One oxidation was made wherein concentration of bromine was lowered as a component of the cobalt-manganese-bromine catalyst but in the presence of an addition of hafnium. The absolute concentrations of manganese and cobalt were increased. The mole ratio of bromine to total metals present, cobalt plus manganese, was 1.0:4.35. Methyl bromide emission was 8.1 ppmw.

Details are in Table VII.

TABLE VII

Production of Bromine Compounds In Vent Gas - Oxidation of p-Xylene

| Case | Br/Mn + Co Catalyst (Moles) (1) | Br Conc. (Moles) (ppmw) | Co Conc. (ppmw) (3) | Reaction Temp. °C. | $CO_x$ (4) | MeBr Vent Gas (ppmv) |
|---|---|---|---|---|---|---|
| Control | 0.47 | 1.0:2.13(2) 320(5) | 257 | 400 | 0.296 | 10.1 |
| Low Br | 0.26 | 1.0:3.85(2) 237(5) | 369 | 400 | 0.353 | 12.7 |
| Low Br Plus Hf | 0.23 | 1.0:4.35(2) 187(5) | 302 | 401 | 0.312 | 8.1 |

Notes:
(1) Moles Br: moles Co plut Mn
(2) Moles Br: moles metal Co and Mn in catalyst system
(3) Co concentration in mother liquor effluent
(4) Moles $CO_x$ produced per mole of p-xylene oxidized
(5) Br concentration, ppmw, in mother liquor The above data show that a low mole ratio of bromine to metals in the catalyst system (2), and a low bromine concentration in ppmw, (5) in the mother liquor plus addition of hafnium to a catalyst system comprising cobalt-manganese-bromine reduces production of bromine compounds in the vent gas, thus reducing loss of bromine compounds with consequent reduced corrosion of equipment caused by the presence of bromine. Bromine emission is also reduced.

The data indicate that emission of bromine compounds increases in the presence of low bromine concentration and a low bromine to metals ratio in the catalyst system in the absence of hafnium. Addition of hafnium combined with a low bromine concentration and a low bromine to metals ratio can lower emission of bromine compounds. A mole ratio of bromine to metals of less than about 1.0:2.13 in a catalyst system comprising cobalt-manganese-bromine wherein hafnium is present in the mother liquor of up to about 250 ppmw therefore can reduce bromine compound emissions in oxidation of p-xylene.

What is claimed is:

1. A process for oxidizing polymethylbenzenes with molecular oxygen to benzene polycarboxylic acids in a reaction solvent comprising a $C_2$–$C_6$ aliphatic carboxylic acid or a mixture of a $C_2$–$C_6$ aliphatic carboxylic acid and water under liquid phase conditions at temperatures in the range of 100° to 275° C., which comprises conducting said oxidation in the presence of a catalyst consisting essentially of a source of soluble hafnium and a catalyst system selected from the group consisting of cobalt-manganese-bromine, manganese-bromine, and cobalt-bromine wherein said soluble hafnium is present in an amount equal to or less than 250 parts per million by weight of total mother liquor content and said catalyst system contains for each gram mole of such methylbenzene from 1.0 to 20.0 milligram atoms of the transition metal manganese or cobalt or total of cobalt and manganese and from 0.2 to 10.0 milligram atoms of bromine, and reactor product cake of said process contains less than 0.3 ppmw of said hafnium after an acetic acid wash or a water wash or an acetic acid-water wash.

2. The process of claim 1 wherein acetic acid is used as the reaction solvent and air as a source of molecular oxygen.

3. The process of claim 2 wherein said polymethylbenzene is p-xylene and said p-xylene is oxidized to terephthalic acid.

4. The process of claim 2 wherein said polymethylbenzene is o-xylene and said o-xylene is oxidized to phthalic acid.

5. The process of claim 2 wherein said polymethylbenzene is pseudocumene and said pseudocumene is oxidized to trimellitic acid.

6. The process of claim 1 wherein said polymethylbenzene is durene and said durene is oxidized to pyromellitic acid.

7. The process of claim 1 wherein said polymethylbenzene is m-xylene and said m-xylene is oxidized to isophthalic acid.

8. The process of claim 1 wherein the ratio of bromine to total metals of hafnium, cobalt and manganese is from 0.1:1.0 to 10.0:1.0.

9. The process of claim 1 wherein said soluble hafnium is present in said mother liquor in an amount equal to or less than 250 parts per million, mole ratio of bromine to metals in said catalyst system is less than 1.0:2.13 whereby production of bromine compounds in vent gases from said oxidation is decreased.

10. The process of claim 1 wherein concentration of catalyst metals consisting of cobalt and manganese of said catalyst system is reduced by at least 12 wt % in the presence of at least 30 ppmw of a source of soluble hafnium without loss of catalyst activity.

11. The process of claim 1 wherein said polymethylbenzenes are oxidized to corresponding aromatic acids wherein the mole ratio of said soluble hafnium to said catalyst system consisting of cobalt plus manganese plus bromine is from about 1:20 to about 1:600 and mole ratio of cobalt to manganese is in the range of from about 4:1 to about 0.2:1.0.

12. The process of claim 1 wherein said polymethylbenzenes are oxidized to corresponding aromatic acids wherein the weight ratio of said soluble hafnium to said catalyst system consisting of cobalt plus manganese plus bromine is about 1 part hafnium to about 50 parts total cobalt plus manganese plus bromine, and mole ratio of cobalt to manganese is in the range of from about 4:1 to about 0.2:1.0.

13. A process for oxidizing o-xylene with molecular oxygen to phthalic anhydride in a reaction solvent comprising a $C_2$–$C_6$ aliphatic carboxylic acid or a mixture of a $C_2$–$C_6$ aliphatic carboxylic acid and water under liquid phase conditions at temperatures in the range of 100° to 275° C., which comprises conducting said oxidation in the presence of a catalyst consisting essentially of a source of soluble hafnium and a catalyst system selected from the group consisting of cobalt-manganesebromine, manganese-bromine, and cobalt-bromine wherein said soluble hafnium is present in an amount equal to or less than 250 parts per million by weight of total mother liquor content and said catalyst system contains for each gram mole of such o-xylene from 1.0 to 20.0 milligram atoms of the transition metal manganese or cobalt or total of cobalt and manganese and from 0.2 to 10.0 milligram atoms of bromine, and reactor product cake of said process contains less than 0.3 ppmw of said hafnium after an acetic acid wash or a water wash or an acetic acid-water wash.

14. A process for oxidizing durene with molecular oxygen to pyromellitic anhydride in a reaction solvent comprising a $C_2$–$C_6$ aliphatic carboxylic acid or a mixture of a $C_2$–$C_6$ aliphatic carboxylic acid and water under liquid phase conditions at temperatures in the range of 100° to 275° C., which comprises conducting said oxidation in the presence of a catalyst consisting essentially of a source of soluble hafnium and a catalyst system selected from the group consisting of cobalt-manganese-bromine, manganese-bromine, and cobalt-bromine wherein said soluble hafnium is present in an amount equal to or less than 250 parts per million by weight of total mother liquor content and said catalyst system contains for each gram mole of such durene from 1.0 to 20.0 milligram atoms of the transition metal manganese or cobalt or total of cobalt and manganese and from 0.2 to 10.0 milligram atoms of bromine, and reactor product cake of said process contains less than 0.3 ppmw of said hafnium after an acetic acid wash or a water wash or an acetic acid-water wash.

15. A process for oxidizing durene with molecular oxygen to pyromellitic dianhydride in a reaction solvent comprising a $C_2$–$C_6$ aliphatic carboxylic acid or a mixture of a $C_2$–$C_6$ aliphatic carboxylic acid and water under liquid phase conditions at temperatures in the range of 100° to 275° C., which comprises conducting said oxidation in the presence of a catalyst consisting essentially of a source of soluble hafnium and a catalyst system selected from the group consisting of cobalt-manganese-bromine, manganese-bromine, and cobalt-bromine wherein said soluble hafnium is present in an amount equal to or less than 250 parts per million by weight of total mother liquor content and said catalyst system contains for each gram mole of such durene from 1.0 to 20.0 milligram atoms of the transition metal manganese or cobalt or total of cobalt and manganese and from 0.2 to 10.0 milligram atoms of bromine, and reactor product cake of said process contains less than 0.3 ppmw of said hafnium after an acetic acid wash or a water wash or an acetic acid-water wash.

* * * * *